United States Patent [19]
Marchand et al.

[11] 4,151,252
[45] Apr. 24, 1979

[54] DEVICE FOR THE ANALYSIS OF SAMPLES BY MEASUREMENT OF THE HEAT FLUX RELEASED AT THE TIME OF CONTACTING OF EACH SAMPLE WITH A REAGENT

[75] Inventors: Joseph Marchand, Pont Saint Esprit; André Roger, Bagnols sur Ceze, both of France

[73] Assignee: Commissariat a l'Energie Atomique, Paris, France

[21] Appl. No.: 832,455

[22] Filed: Sep. 12, 1977

[30] Foreign Application Priority Data

Sep. 13, 1976 [FR] France .................................. 76 27468

[51] Int. Cl.² ............................................. G01N 25/20
[52] U.S. Cl. ..................................................... 422/51
[58] Field of Search ............. 23/253 R, 254 R, 230 R; 204/1, 195 T; 73/190 R

[56] References Cited
U.S. PATENT DOCUMENTS

| 3,154,477 | 10/1964 | Kesler | 23/253 R |
| 3,160,477 | 12/1964 | Wasilewski | 23/253 R |
| 3,519,547 | 7/1970 | Paulik et al. | 23/255 E |
| 3,888,726 | 6/1975 | Hultman | 23/230 R X |

Primary Examiner—R. E. Serwin
Attorney, Agent, or Firm—William B. Kerkam, Jr.

[57] ABSTRACT

A heat-insulating enclosure contains temperature-regulating means and open-topped vessels each containing a sample of predetermined volume and transferred from a storage position to an analysis position in which a predetermined volume of reagent solution is contacted with the sample. Means are provided for detecting the respective temperatures of the sample and the reagent, for detecting the heat flux released and limiting thermal variations in the vicinity of each sample.

9 Claims, 2 Drawing Figures

DEVICE FOR THE ANALYSIS OF SAMPLES BY MEASUREMENT OF THE HEAT FLUX RELEASED AT THE TIME OF CONTACTING OF EACH SAMPLE WITH A REAGENT

This invention relates to a device for analyzing samples by measuring the heat flux which is released when each sample is contacted with a reagent.

The device in accordance with this invention is more particularly intended for the enzymatic determination of a substrate contained in samples of blood serum.

It is recalled that, in the case of a device for sample analysis employed in clinical chemistry especially for the analysis of blood serums, it can be of primary interest to carry out successive determinations of samples of small volume at a high rate.

From this point of view, conventional heat-conduction calorimeters cannot be employed in clinical chemistry by reason of the lengths of time required for establishing thermal equilibrium prior to analysis of a sample.

Thus special devices have been designed and developed prior to the invention for the analysis of samples in clinical chemistry. These devices usually have a system for contacting samples with a reagent. This system is suitably designed and associated with a system for detecting the flux released at the time of contacting which has low thermal inertia.

All the devices of the type mentioned above and designed prior to the invention have a disadvantage in that they do not offer a sufficient degree of reliability and make it possible to obtain only a limited rate of analysis while requiring excessive times of establishment of equilibrium of the sample and of the reagent to be contacted.

One device is known, for example, in which contacting of samples with the enzymatic reagent is carried out by fixing this latter on a support attached to the detector. This device has a disadvantage in that it does not permit satisfactory successive determinations since the enzymatic reagent is retained from one determination to the next.

A device is also known in which contacting is carried out by non-continuous mixing of volumes of serum and reagent which have previously been equilibrated.

The disadvantage of this device lies in the fact that it requires an excessive volume of serum for each determination and calls for complex arrangements for the circulation of the serum and the reagent and for the rinsing operations.

The precise aim of the present invention is to provide a device for sequential analysis of samples by measurement of the heat flux released at the time of contacting of each sample with a reagent, thereby overcoming the disadvantages mentioned in the foregoing.

The device in accordance with this invention essentially comprises:

1. Within a heat-insulating enclosure:
   means for regulating the temperature within said enclosure,
   open-topped electrically insulating vessels each containing a sample of predetermined volume and having low thermal inertia,
   vessel-positioning means for displacing each vessel aforesaid between a storage position and an analysis position,
   a reservoir for the reagent solution,
   means for distributing the reagent solution which are capable of distributing a predetermined volume of said reagent within each vessel aforesaid in the analysis position,
   means for detecting the respective positions of the sample contained within the vessel in the analysis position and the volume of reagent which is intended to be contacted therewith,
   thermoelectric means having low thermal inertia for detecting the heat flux liberated at the time of contacting of each sample with the reagent,
   means for ensuring discharge of the heat flux which are capable of limiting thermal variations within the zone surrounding each vessel aforesaid in the analysis position.

2. Externally of said enclosure,
   means for measuring the thermal equilibrium between the vessel sample in the analysis position and the volume of reagent which is intended to be contacted therewith,
   means for measuring the heat flux released at the time of contacting of each sample with the reagent,
   means which serve to control said means for distributing the solution of said reagent,
   means which serve to control said means for positioning said vessels.

The device in accordance with the invention as defined above in its essential features has the main advantage of permitting the analysis of a plurality of samples such as samples of blood serum at a high rate.

It is in fact noted that this device advantageously associates the following means:
   a system for the distribution of pre-equilibrated samples comprising the sample vessels and the means aforesaid for positioning said samples and permitting the high-speed analysis of samples having a small volume which is usually lower than 100 $\mu$l in the case of enzymatic determinations by carrying out reactions which are rapid and total in the presence of an excess quantity of enzymatic reagent,
   a heat flux detector having low thermal inertia and rapid return to equilibrium,
   means for ensuring the discharge of the heat flux, said means being intended to permit rapid thermal equilibrium of each sample and of the volume of reagent to be contacted therewith while limiting thermal variations in the vicinity of said samples.

In accordance with the invention, said vessels are preferably constituted by cups of anodized aluminum which may or may not be inserted in a metallic block and are uniformly disposed on at least one supporting strip so arranged as to ensure a thermal bond between the detector and each cup and constituting said vessel-positioning means in conjunction with a system for initiating the step-by-step displacement of said strip.

Moreover and in accordance with the invention, said means for detecting the heat flux comprise two thermopiles having low thermal inertia and high thermoelectric power, each thermopile being preferably constituted by a series arrangement of thermocouples of bismuth telluride for example which may be either positively or negatively doped.

In accordance with a preferential arrangement of the invention, said thermopiles are arranged within said enclosure in such a manner as to ensure that each vessel in the analysis position is interposed between said thermopiles in contact with one thermopile and separated from the other by a heat insulator.

Furthermore and in accordance with the invention, said heat flux discharge means which are capable of limiting the thermal variations within the zone located next to a vessel in the analysis position are preferably constituted by a metallic block having a high heat capacity for accommodating said heat flux detection means with good thermal contact and permitting on the one hand the introduction and extraction of a vessel which is intended to be placed within said block in the analysis position and on the other hand the distribution of a predetermined volume of reagent within said vessel in the analysis position.

In accordance with a preferential arrangement of the invention, said block accommodates that portion of said reagent distribution means which contains the volume of reagent to be introduced into the vessel which has just been placed in the analysis position.

In accordance with the invention, said block has two openings through which said strip for supporting said vessels is permitted to pass, said openings being closed-off by means of heat-insulating members when a vessel is located within said block in the analysis position, said heat-insulating members being carried by said strip and providing separations between the vessels.

The device in accordance with the invention has the advantage of readily permitting automatic operation. To this end, the device further comprises two groups of means which are associated respectively with said means for measuring the thermal equilibrium and with said means for detecting the heat flux in order to initiate the operation of said means which serve to control the means for positioning the vessels and distributing the enzyme solution.

Further distinctive features and advantages of the present invention will become more readily apparent from the following description of one exemplified embodiment of the device in accordance with the invention which is given by way of illustration but not in any sense by way of limitation, reference being made to the accompanying diagrammatic figures, wherein.

Although the practical application of the device in accordance with the invention is not limited to enzymatic determination of a substrate contained in samples of blood serum, the following description relates to this type of analysis by way of illustration.

Figure 1:
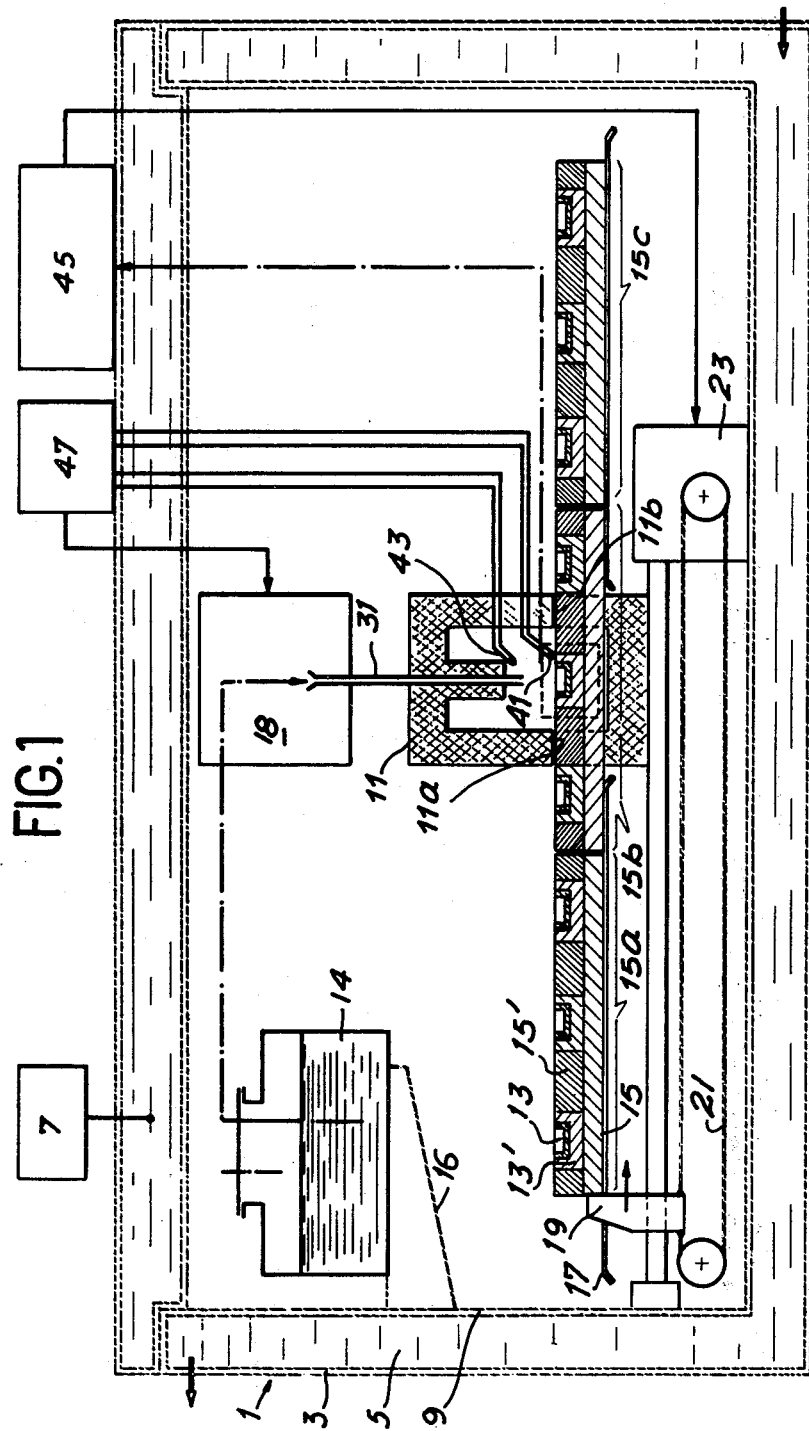
FIG. 1 is a general vertical sectional view of the device in accordance with the invention.

FIG. 1 shows that the device in accordance with the invention is constituted by two assemblies which are located internally and externally with respect to a heat-insulating enclosure 1. The inner assembly comprises in particular on the one hand systems for the distribution of samples of serum and fractions of an enzyme solution and on the other hand a system for the detection of the heat fluxes generated by contacting the samples with the enzyme and the outer assembly which is provided with systems for measuring the fluxes and controlling the systems of the inner assembly.

It is worthy of note that, from the exterior towards the interior, said enclosure 1 is successively delimited by an insulating wall 3 which is intended to limit heat exchanges with the exterior, a volume of water 5 regulated by means 7 of known type, a semi-insulating wall 9 for permitting removal of the heat generated within the enclosure by said volume of water 5 while damping surges in the regulation of the water. Said volume of water 5 is preferably regulated at 25° C. to within ±0.01° C. and said semi-insulating wall 9 is preferably constituted by a sheet of polyethylene lined with Teflon.

It is observed in FIG. 1 that the internal space of said enclosure in which the air is removed to the maximum extent in order to limit heat-transfer times is subdivided by a wall 11 formed of material having a high heat capacity such as aluminum into two zones located externally and internally with respect to said wall 11 so as to constitute respectively a pre-equilibration zone P and an analysis zone A.

Provision is made within said pre-equilibration zone P for a plurality of cups 13 formed preferably of anodized aluminum and each containing a sample of blood serum having a given volume, an enzyme solution reservoir 14 placed on a support bracket 16 which is rigidly fixed to the enclosure 1 and a distributor 18 for predetermined fractions of 50 to 100 μl of said enzyme solution.

In more precise terms, said cups 13 which are each inserted in a metallic support 13' of aluminum, for example, are supported by metallic strips 15 which are preferably also formed of aluminum. Said strips 15 are intended to be displaced horizontally along ramps 17 for guiding said strips in translational motion through said analysis zone A under the action of a push-plate 19 which is actuated by a stepping motor 23 by means of cables 21. Said strips 15 which are capable of traversing said zone A through the openings 11a and 11b formed in said wall 11 thus make it possible to position each cup 13 in the zone A, said cups being located in uniformly spaced relation on a strip 15.

It is noted that said cups are separated on a strip 15 by heat-insulating members 15', said members being capable of closing-off said openings 11a and 11b when a cup is in the position of analysis within said zone A.

Figure 2:
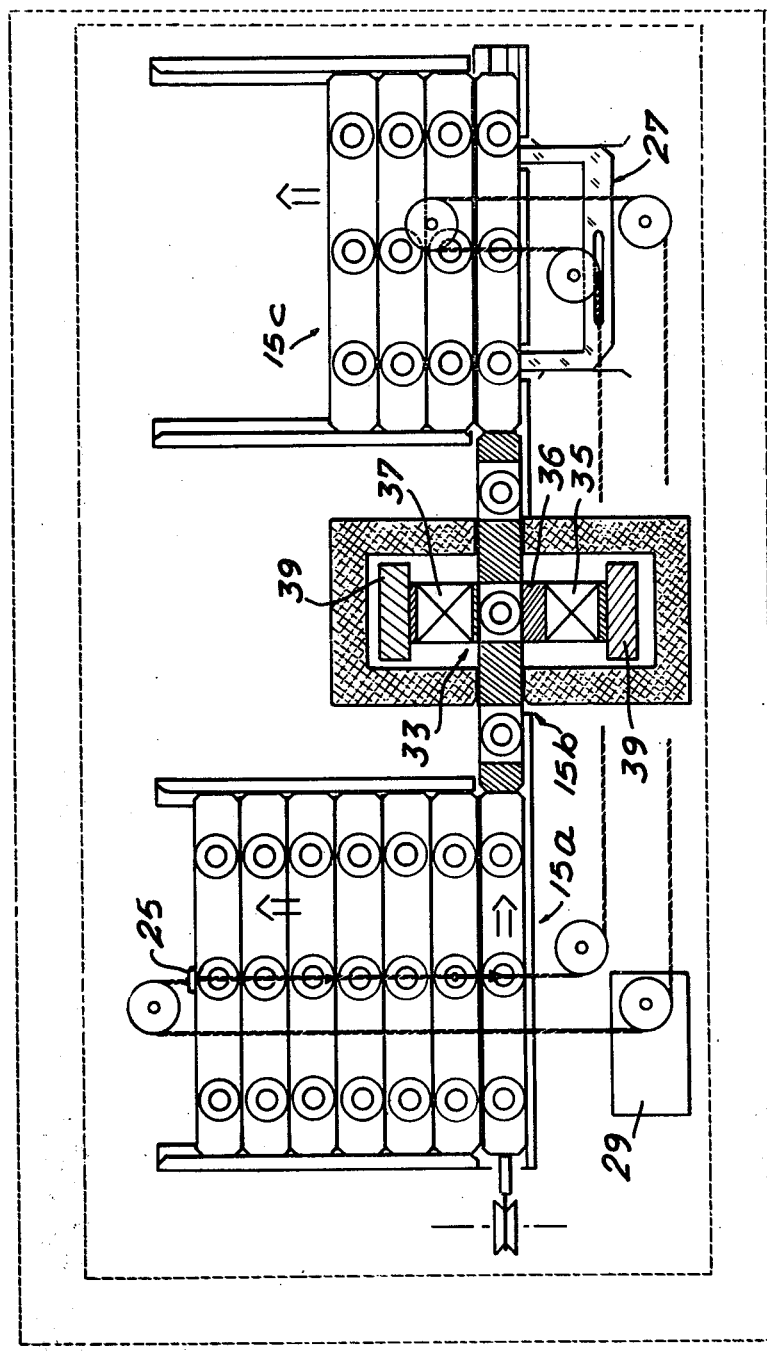
FIG. 2 is a horizontal sectional view of the device in accordance with the invention.

It can also be noted from FIGS. 1 and 2 that three separate strips are aligned on said guide ramps 17 in order to carry out at a suitable rate the unloading of the end strip 15c and the loading of a fresh strip 15a under the action of push-plates 25 and 27 actuated by a stepping motor 29.

It is also observed that, for the introduction of a fraction of enzyme solution into each cup 13 after positioning of this latter within said zone A, the discharge tube 31 of said distributor 18 passes through said metallic wall 11. Said wall 11 has a shape such as to imprison that portion of said discharge tube 31 which contains the fraction of solution to be distributed within the cup 13 which has just been positioned within said zone A. Thus the wall 11 formed of material having high heat capacity permits on the one hand satisfactory flow of the heat flux released as a result of proportioning of a sample towards the volume of water 5 and on the other hand rapid equilibration of the sample and of the reagent of the following proportioning operation. Moreover, it is apparent from FIG. 2 that a detector 33 for the heat fluxes released at the time of enzymatic determination of each sample is placed within said analysis zone A. More precisely, said detector 33 is constituted by two thermopiles 35 and 37 mounted in opposition. Each thermopile is constituted by a series connection by means of copper strips, of positively or negatively doped thermocouples formed preferably of bismuth telluride, this assembly being carried by a plate 39 of anodized aluminum.

By way of example, it is possible to employ thermopiles designated commercially as modules P4 by CIT Alcatel and consisting of eight positively or negatively doped thermocouples of bismuth telluride.

Thus the thermopiles 35 and 37 advantageously have low thermal inertia and high thermoelectric power. The threshold of detection of the detector 33 as thus constituted is in the vicinity of 3 mcal.

It is observed in addition that said thermopiles 35 and 37 are placed symmetrically on each side of the passageway provided for a strip 15, the thermopile 35 being fixed on a heat-insulating block 36.

It is also worthy of note that said thermopiles 35 and 37 are arranged within said zone A in such a manner as to ensure that a cup 13 in the analysis position is in contact with the thermopile 37 and the heat-insulating block 36 which is fixed on the thermopile 35.

Furthermore, FIG. 1 shows that two thermocouples 41 and 43 which are mounted in opposition are placed respectively in the proximity of the cup contained in the zone A and of the discharge tube 31 of the distributor 18. The thermocouples aforesaid are intended to control the temperature difference between a sample and the volume of enzymatic reagent to be introduced into this latter. The temperature difference is intended to be smaller than $10^{-2}$° C. in order to carry out an analysis.

The detector 33 and the thermocouples 41 and 43 are connected to suitable measuring devices 45 and 47 by means of lead-wires which have the smallest possible diameter.

In order to permit of automatic operation, the device described in the foregoing is advantageously provided in addition with electrical means whereby the measuring device 45 controls the motors 23 and 29 for step-by-step displacement of the cups 13 and the measuring device 47 controls the distributor 18 for delivering predetermined fractions of enzyme solution.

Taking the foregoing description into account, the principle of operation of the device which is rendered automatic by suitable means is as follows:

after positioning of a cup 13 within the analysis zone A, the thermocouples 41 and 43 serve to control the establishment of thermal equilibrium of the sample contained in said cup and of the volume of enzymatic reagent to be contacted with this latter, initial operation of the distributor 18 when the signal emitted by the thermocouples 41 and 43 is representative of the desired equilibrium between the sample and the reagent corresponding to a temperature difference between these latter which is smaller than $10^{-2}$° C. initiates the enzymatic reaction; the heat flux which is then released passes through the thermopile 37, then flows through the wall 11 from the zone A to the volume of regulated water 5, start-up of the motor 23 and if necessary of the motor 29 when the signal emitted by the detector 33 is representative of its return to equilibrium permits positioning of the following cup within the zone A.

It should be pointed out that the device described in the foregoing makes it possible to analyze at least ten samples of serum per hour with a degree of accuracy of the order of 5%, the volume of each sample being within the range of 50 to 100 μl.

It can also be noted that the value of the heat flux of the rapid and total reactions carried out in zone A can be deduced from the amplitude of the signal emitted by the detector 33 which has a sufficiently short response time.

The value of the flux can also be deduced from the integration of the signal emitted by the detector by adopting a fixed measurement period.

Control of the detector 33 of the device is effected by means of an electric resistor placed within a cup 13 so as to generate a predetermined value of heat energy within this latter.

Moreover, the thermal operation of the measuring system can be controlled by the detection of the heat flux released by a known chemical reaction.

The description which now follows and which is given by way of illustration provides one example of application of the device in accordance with the invention for the determination of urea in the blood as a result of hydrolysis of the urea by urease.

There were placed within the enclosure 1 on the one hand cups which each contained for the purpose of calibration 100 μl of a solution of urea having predetermined and variable concentrations and, on the other hand, a cup containing 100 μl of a blood serum to be analyzed, said serum to be analyzed being taken from a reserve supply of 20 ml of 20 normal serums.

There was introduced into the distributor 18 a solution of urease having 65 international units per ml of phosphate buffer solution containing 0.05 m/l having a pH value of 6.5 and containing 10 g/l of EDTA.

The results obtained were as follows:

in the case of a urea solution containing 1.56 g/l, the amplitude of the signal delivered was 19.8 μV±0.02 μV, in the case of a urea solution containing 0.8 g/l, the amplitude of the signal delivered was 13.4 μV±0.02 μV, in the case of a urea solution containing 0.33 g/l, the amplitude of the signal delivered as 10.2 μV±0.02 μV.

The urea concentration of the serum to be analyzed as given by the device in accordance with the invention was 0.32 g/l whilst the concentration of said serum as given by the Boehringer analysis was 0.33 g/l.

Similarly, the device in accordance with the invention can advantageously be employed for the analysis of glucose, uric acid, cholesterol contained in samples of blood serum which may or may not have been pretreated.

What we claim is:

1. Apparatus for the analysis of samples by measurement of the heat flux liberated during contact of each of the samples with a reagent comprising a thermally insulated enclosure, means for regulating the temperature in said enclosure, a wall in said enclosure defining in said enclosure a first sample analysis zone within said wall, a second zone for thermal equilibrium of the samples and the reagent external of said wall in said enclosure, said wall having a high calorific capacity providing flow of the heat flux liberated in said analysis zone toward said enclosure, vessels open at their upper extremities each containing a sample for analysis of determined volume, said vessels having low thermal inertia and being electrically insulated, means for positioning said vessels and for displacing each of said vessels between a storage position in said equilibrium zone and an analysis position in said first analysis zone, said means thermally isolating the vessel in analysis position from the vessels in storage position, a reservoir for a reagent solution in said second equilibrium zone, means for distributin said reagent solution into a vessel in analysis position providing a predetermined volume of said reagent solution, at least a part of said distribution means being located in said wall for the thermal equilibrium of the sample in analysis position with said predetermined volume of reagent solution to be brought into contact with the sample, means in said first zone for detecting the respective temperatures of the sample in the vessel in analysis position and of the volume of reagent solution to be brought into contact with the sample, thermoelectric means in said first zone of low thermal inertia detecting the heat flux liberated during the contact of each of the samples with the reagent solution, means outside of said enclosure electrically connected to said detecting means for measuring the thermal equilibrium between the sample in the vessel in analysis position and the volume of reactant solution in contact therewith, means outside of said enclosure electrically connected to said thermoelectric means for measuring the heat flux liberated during the contact of each of the samples with the reagent solution, means outside of said enclosure for control of said distribution means of the reagent solution and control means outside said enclosure for controlling said means for positioning said vessels.

2. A device according to claim 1, wherein said vessels are constituted by cups of anodized aluminum.

3. A device according to claim 1, wherein said vessels are constituted by cups of anodized aluminum inserted in aluminum blocks.

4. A device according to claim 1, wherein said vessel-positioning means comprise at least one strip which is guided in translational motion for supporting said vessels and a system for controlling the step-by-step displacement of said strip, said vessels being placed on said strip with a constant pitch.

5. A device according to claim 1, wherein said means for detecting the heat flux comprise two thermopiles mounted in opposition which have low thermal inertia and high thermoelectric power.

6. A device according to claim 5, wherein each thermopile aforesaid is constituted by a series assembly of semiconductor thermocouples.

7. A device according to claim 5, wherein the thermopiles are arranged within said enclosure in such a manner as to ensure that each vessel in the analysis position is interposed between said thermopiles in contact with one of said thermopiles and separated from the other by means of a heat insulator.

8. A device according to claim 1, wherein said block has two openings through which said strip for supporting said vessels is permitted to pass, said openings being closed-off by means of heat-insulating members when a vessel is located within said wall in the analysis position, said heat-insulating members being carried by said strip and providing separations between said vessels.

9. A device for automatic analysis according to claim 1, wherein said device further comprises two groups of means which are associated respectively with said means for measuring the thermal equilibrium and with said means for detecting the heat flux in order to initiate the operation of said means which serve to control the means for positioning the vessels and distributing the reagent solution.

* * * * *